US008354537B2

(12) United States Patent
Arad et al.

(10) Patent No.: US 8,354,537 B2
(45) Date of Patent: Jan. 15, 2013

(54) R,R¹-ATRACURIUM SALTS

(75) Inventors: Oded Arad, Rehovot (IL); Ofer Sharon, Petach Tikvah (IL); Elena Ostrovsky, Rishon Le-zion (IL)

(73) Assignee: CHEMAGIS Ltd., Bnei Brak (IL)

( * ) Notice: Subject to any disclaimer, the term of this patent is extended or adjusted under 35 U.S.C. 154(b) by 217 days.

(21) Appl. No.: 12/739,789

(22) PCT Filed: Oct. 7, 2008

(86) PCT No.: PCT/IL2008/001329
§ 371 (c)(1),
(2), (4) Date: May 17, 2010

(87) PCT Pub. No.: WO2009/057086
PCT Pub. Date: May 7, 2009

(65) Prior Publication Data
US 2010/0234602 A1 Sep. 16, 2010

Related U.S. Application Data

(60) Provisional application No. 60/983,440, filed on Oct. 29, 2007.

(51) Int. Cl.
*C07D 401/12* (2006.01)
(52) U.S. Cl. .................................................. 546/140
(58) Field of Classification Search .................. None
See application file for complete search history.

(56) References Cited

U.S. PATENT DOCUMENTS

| | | | |
|---|---|---|---|
| 4,179,507 A | 12/1979 | Stenlake et al. | |
| 4,491,665 A | 1/1985 | El-Sayad et al. | |
| 4,701,460 A | 10/1987 | El-Sayad et al. | |
| 4,761,418 A | 8/1988 | Swaringen, Jr. et al. | |
| 4,851,537 A | 7/1989 | Noyori et al. | |
| 4,988,815 A | 1/1991 | Andre et al. | |
| 5,240,939 A | 8/1993 | Demko | |
| 5,453,510 A | 9/1995 | Hill et al. | |
| 5,556,978 A | 9/1996 | Hill et al. | |
| 5,684,154 A | 11/1997 | Chamberlin et al. | |
| 6,015,903 A | 1/2000 | Viergutz et al. | |
| 6,177,445 B1 | 1/2001 | Bigham et al. | |
| 6,187,789 B1 | 2/2001 | Bigham et al. | |
| 6,830,933 B2 | 12/2004 | Lemmens et al. | |
| 7,265,099 B1 | 9/2007 | Bom et al. | |
| 2006/0009485 A1 | 1/2006 | Friedman et al. | |
| 2008/0139482 A1 | 6/2008 | Savarese | |
| 2009/0156562 A1 | 6/2009 | Winch | |
| 2010/0016596 A1 | 1/2010 | Pozzoli et al. | |
| 2010/0087650 A1 | 4/2010 | Ostrovsky et al. | |
| 2010/0099878 A1 | 4/2010 | Arad et al. | |
| 2010/0168431 A1 | 7/2010 | Naddaka et al. | |
| 2010/0174082 A1 | 7/2010 | Arad et al. | |
| 2010/0184988 A1 | 7/2010 | Naddaka et al. | |
| 2010/0256381 A1 | 10/2010 | Arad et al. | |
| 2010/0298570 A1 | 11/2010 | Segnalini et al. | |
| 2011/0185796 A1 | 8/2011 | Arad et al. | |

FOREIGN PATENT DOCUMENTS

| | | |
|---|---|---|
| CN | 101084896 A | 12/2007 |
| CN | 101337935 A | 1/2009 |
| CN | 101337936 A | 1/2009 |
| CN | 101475530 A | 7/2009 |
| CN | 101845017 A | 9/2010 |
| EP | 0 219 616 | 4/1987 |
| EP | 0219616 | 4/1987 |
| WO | WO 92/00965 A1 | 1/1992 |
| WO | WO 98/42675 A1 | 10/1998 |
| WO | WO 2007/091753 A1 | 8/2007 |
| WO | WO 2008/107887 A2 | 9/2008 |
| WO | WO 2008/117271 A1 | 10/2008 |
| WO | WO 2008/132746 A1 | 11/2008 |
| WO | WO 2008/132748 A1 | 11/2008 |
| WO | WO 2008/155752 A1 | 12/2008 |
| WO | WO 2009/007946 A1 | 1/2009 |
| WO | WO 2009/106547 A1 | 9/2009 |
| WO | WO 2009/133556 A2 | 11/2009 |
| WO | WO 2010/128518 A2 | 11/2010 |
| WO | WO 2010/128519 A1 | 11/2010 |

OTHER PUBLICATIONS

Lindon et al. "Directly coupled HPLC-NMR and HPLC-NMR-MS in pharmaceutical research and development," Journal of Chromatography B : Biomedical Applications, Elsevier Science Publishers, NL, vol. 748, No. 1, pp. 233-258 (Oct. 1, 2000).

Liu et al. "High-performance liquid chromatography of atracurium besylate," Yao Hsueh Hsueh Pao—Acta Pharmaceutica Sinica, Beijing, CN, vol. 29, No. 1, pp. 68-73 (Jan. 1, 1994).

Mistry et al. "Directly Coupled Chiral HPLC-NMR and HPLC-CD Spectroscopy as Complementary Methods for Structural and Enantiomeric Isomer Identification: Application to Atracurium Besylate," Analytical Chemistry, vol. 71, No. 14, pp. 2838-2843 (1999).

Nehmer "Separation of cis-cis, cis-trans and trans-trans isomers of (.+−.)-atracurium besylate and cis and trans isomers of its major quaternary decomposition products and related impurity by reversed-phase high-performance liquid chromatography," Journal of Chromatography, vol. 457, pp. 127-135 (1988).

Stenlake et al: "Biodegradable Neuromuscular Blocking Agents 6. Stereochemical Studies on Atracurium and Related Polyalkylene Diesters," European Journal of Medicinal Chemistry, Editions Scientifique Elsevier, Paris, FR, vol. 19, No. 5, pp. 441-450 (Jan. 1, 1984).

Stenlake et al., "Neuromuscular Block Agents: Some approaches to short acting compounds," European Journal of Medicinal Chemistry, vol. 27, No. 5, pp. 463-477 (1992).

International Search Report for PCT/IL2008/000291 mailed Jul. 4, 2008.

International Search Report for PCT/IL2008/000290 mailed Jul. 7, 2008.

*Primary Examiner* — Zinna Northington Davis
(74) *Attorney, Agent, or Firm* — Leydig, Voit & Mayer, Ltd.

(57) ABSTRACT

The present invention provides R,R'-atracurium salts, processes for producing and purifying such salts, and methods of using such salts to produce highly pure cisatracurium besylate.

18 Claims, 4 Drawing Sheets

OTHER PUBLICATIONS

International Search Report for PCT/IL2008/000289 mailed Sep. 5, 2008.
International Search Report for PCT/IL2008/000586 mailed Aug. 27, 2008.
International Search Report for PCT/IL2008/000589 mailed Aug. 21, 2008.
International Search Report for PCT/IL2008/001329 mailed Feb. 4, 2009.
ICH Guideline, International Conference on Harmonization of Technical Requirements of Registration of Pharmaceuticals for Human Use (ICH), ICH Q3CR4 residual solvents MEDIA5254 (Feb. 2009).
European Patent Office, International Search Report in International Patent Application No. PCT/IL2008/000590 (Aug. 29, 2008).

R,R¹-ATRACURIUM SALTS

CONTINUING DATA

This application is a 371 of PCT/IL08/01329 filed Oct. 7, 2008 which claims benefit of 60/983,440 filed Oct. 29, 2007.

BACKGROUND OF THE INVENTION

Cisatracurium besylate is the common name of the compound (1R,1'R,2R,2'R)-2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl]-isoquinolinium dibenzenesulfonate, and it is represented by the structural formula (I):

tion, and to provide skeletal muscle relaxation during surgery or mechanical ventilation in the Intensive Care Unit (ICU).

Cisatracurium besylate is marketed in the United States, Europe and other countries by GlaxoSmithKline and Abbott Laboratories under the trade name Nimbex®. Nimbex® is a sterile, non-pyrogenic aqueous solution that is adjusted to pH 3.25 to 3.65 with benzenesulfonic acid. The drug is provided in 2.5 ml, 5 ml and 10 ml vials having strength of 2 mg/ml cisatracurium besylate. A 30 ml vial containing 5 mg/ml cisatracurium besylate is also available.

The potency of the cisatracurium besylate in the formulated, Nimbex® decreases with time at a rate of approximately 5% per year under refrigeration (5° C.). Nimbex should be refrigerated at 2° to 8° C. (36° to 46° F.) to preserve

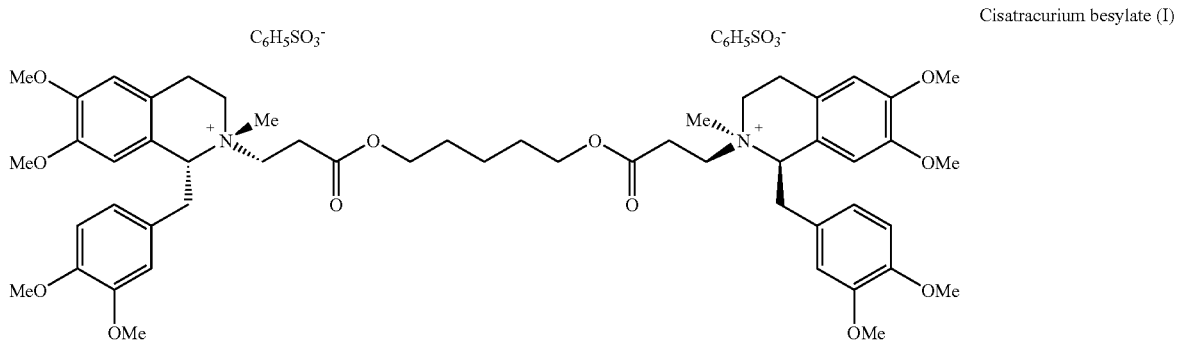

Cisatracurium besylate (I)

Cisatracurium besylate is the 1R-cis,1'R-cis isomer of atracurium besylate, otherwise known as 2,2'-[1,5-pentanediyl-bis[oxy(3-oxo-3,1-propanediyl)]]bis[1-[(3,4-dimethoxyphenyl)methyl]-1,2,3,4-tetrahydro-6,7-dimethoxy-2-methyl]-isoquinolinium dibenzenesulfonate. Atracurium besylate has four chiral centers, which should theoretically allow for 16 possible isomers. Due to the symmetry of the molecule the number of possible isomers is reduced to 10. Cisatracurium besylate is one of 10 isomers of atracurium besylate. See, e.g., J. B. Stenlake et al. in "Biodegradable neuromuscular blocking agents," *Eur. J. Med. Chem.-Chem. Ther.*, vol. 19, issue 5, pp. 441-450 (1984).

Cisatracurium besylate is a nondepolarizing neuromuscular blocking agent indicated for inpatients and outpatients as an adjunct to general anesthesia, to facilitate tracheal intubapotency. The rate of loss in potency increases to approximately 5% per month at 25° C. (77° F.).

U.S. Pat. No. 4,179,507 ("the '507 patent") describes the preparation of a series of bis-veratrylisoquinolinium quaternary ammonium salts, including atracurium besylate. The '507 patent describes the preparation of atracurium besylate by a process that involves coupling (±)-tetrahydropapaverine base (compound II) with 1,5-pentamethylene diacrylate (compound III) and treating the resulting tertiary amine base with oxalic acid to produce N,N'-4,10-dioxa-3,11-dioxotridecylene-1,13-bis-tetrahydropapaverine dioxalate (compound IV). This salt is converted to the free base (compound V), which is treated with methyl benzenesulfonate. The resulting product, atracurium besylate (compound VI), is precipitated and isolated. The process is illustrated below in Scheme 1.

Scheme 1

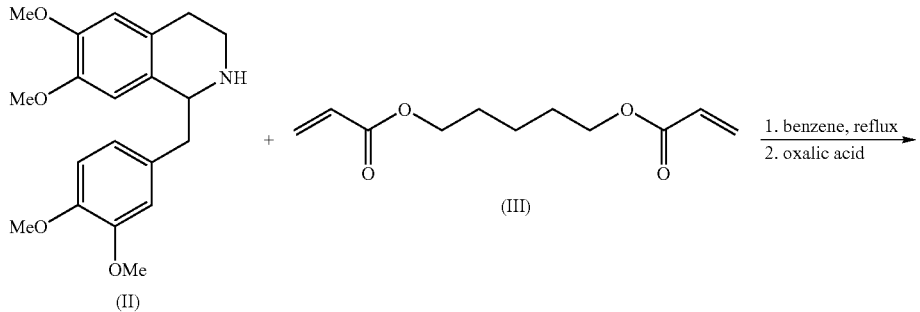

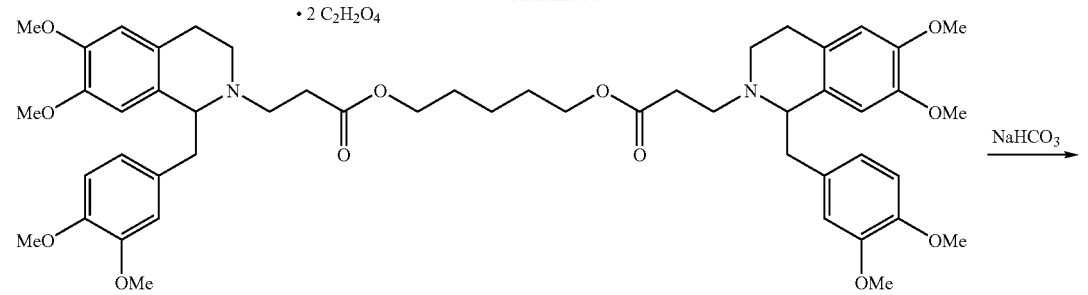

(IV)

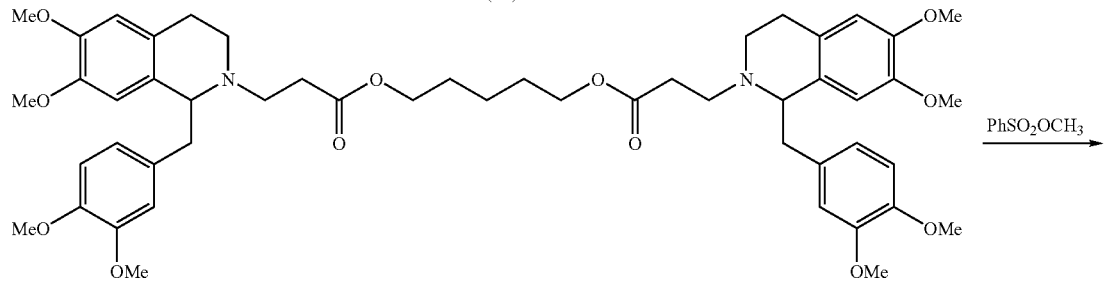

(V)

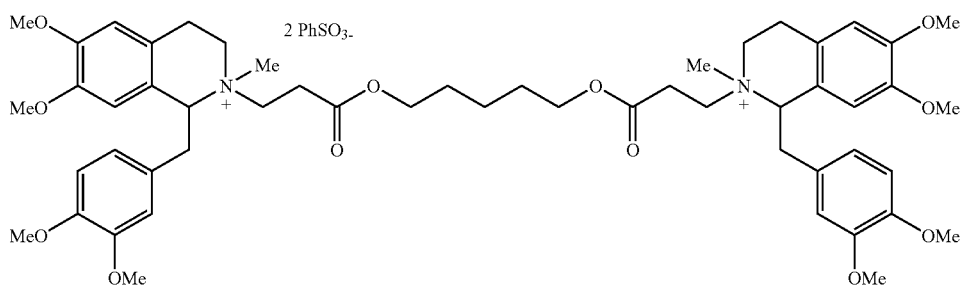

(VI)

European application No. 0219616 ("the '616 application") discloses the synthesis of atracurium chloride. The '616 application describes a process that involves coupling of 1-[(3,4-dimethoxyphenyl)methyl]-3,4-dihydro-6,7-dimethoxy-2(1H)-isoquinolinepropanoic acid (compound VII) with 1,5-pentanediol in the presence of an acid to afford the diester (compound IX). The resulting diester is quaternized with methyl iodide to form atracurium iodide, which is then converted into atracurium chloride by means of anion exchange. The process is illustrated below in Scheme 2.

Scheme 2

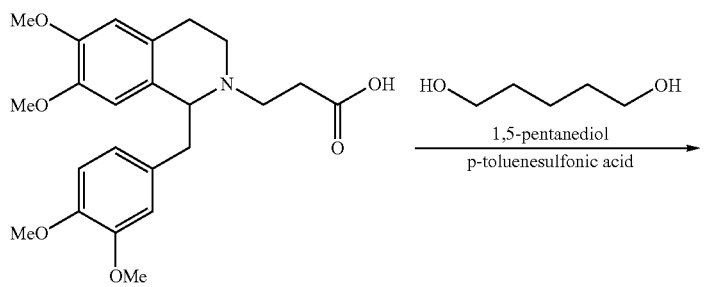

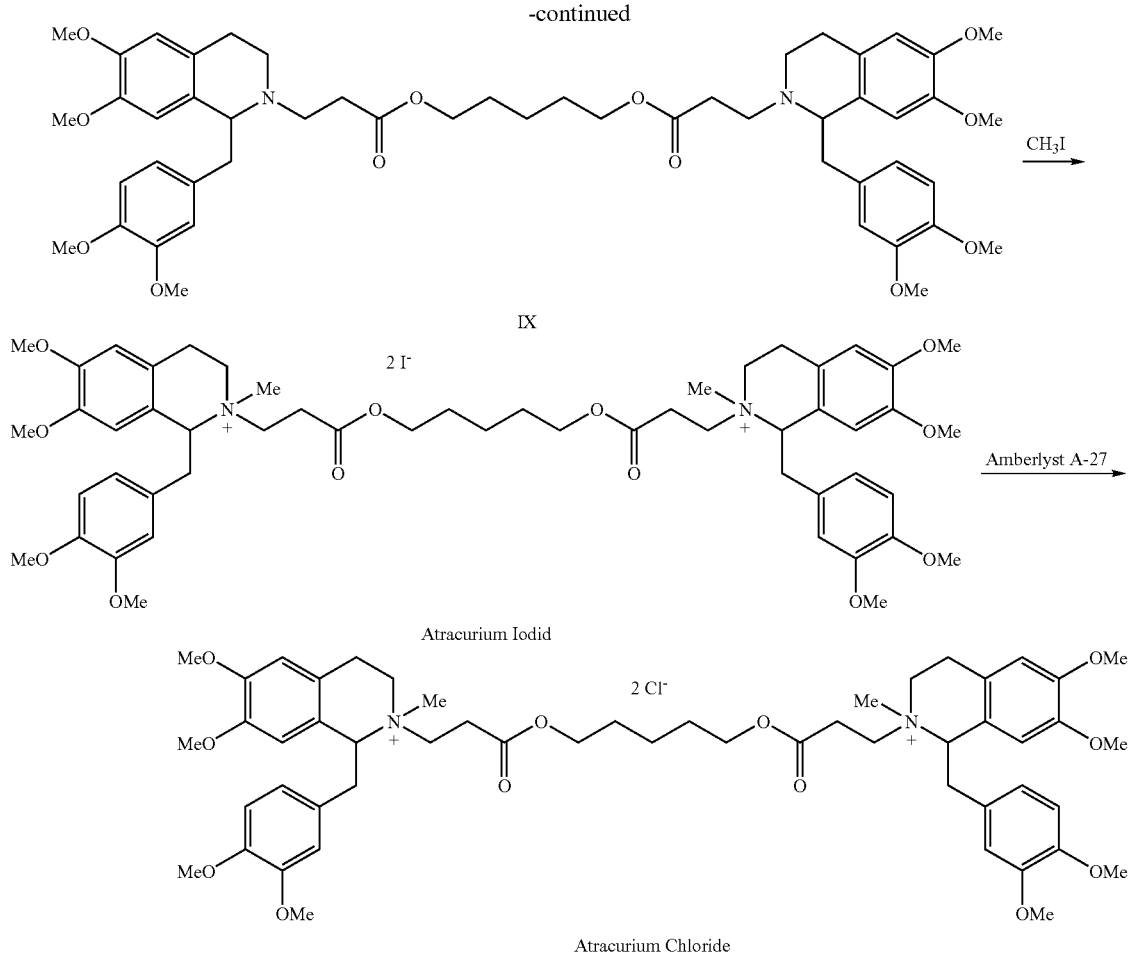

The above-mentioned references do not disclose isomer resolution or how to isolate and purify a single isomer.

U.S. Pat. Nos. 5,453,510 and 5,556,978 ("the '510 patent" and "the '978 patent") disclose cisatracurium besylate. According to these documents, cisatracurium besylate is obtained by a process involving the formation of (R)-tetrahydropapaverine by resolving the racemic mixture of compound (II) with the chiral amino acid N-acetyl-L-leucine and crystallizing from acetone to afford (R)-tetrahydropapaverine-N-acetyl-L-leucinate in 97% yield, which is converted into (R)-tetrahydropapaverine base. The (R)-tetrahydropapaverine obtained is than reacted with 1,5-pentamethylene diacrylate followed by oxalic acid to afford the dioxalate salt of (1R,1'R)-2,2'-(3,11-dioxo-4,10-dioxamidecamethylene)-bis-(1,2,3,4-tetrahydro-6,7-dimethoxy-1-veratrylisoquinoline). Conversion of the dioxalate salt into the free base, followed by treatment with methyl benzenesulfonate, affords a solution of (1R,1'R)-atracurium besylate. After lyophilization a pale yellow solid is obtained containing a mixture of the three isomers: 1R-cis,1'R-cis; 1R-cis,1'R-trans; 1R-trans,1'R-trans (hereinafter referred to as the "R-atracurium besylate mixture") in a ratio of about 58:34:6 respectively. The R-atracurium besylate mixture is subjected to preparative HPLC column chromatography on silica using a mixture of dichloromethane, methanol and benzenesulfonic acid in the ratio of 4000:500:0.25 as the eluent. The fractions containing the required isomer are collected and further processed to afford cisatracurium besylate having an isomeric purity of about 99%.

The above procedure suffers from several disadvantages which render the processes unsuitable for commercial scaling up implementation. One major problem is attributable to the need for HPLC purification, which is undesirable in a large-scale operation because only relatively small amounts of the product can be purified at a time. The method also is expensive, time-consuming and generates large quantities of waste solvents, which raises considerations with regard to the safe disposal of accumulated wastes. Another disadvantage of the above procedures is that cisatracurium besylate may be unstable in the eluent mixture used in the HPLC separation procedure and, thus, can lead to the formation of decomposition products.

Accordingly, there is a need for an improved process for the production of cisatracurium, e.g., cisatracurium besylate, and intermediates therefor, which avoid column chromatography and can be scaled up to facilitate the large scale production of cisatracurium. The present invention provides such a process and intermediates, which can be used for producing highly pure cisatracurium besylate.

BRIEF SUMMARY OF THE INVENTION

The present invention provides novel, stable, isomerically enriched R,R'-atracurium salt mixtures that are useful, e.g., as intermediates for preparing highly pure cisatracurium besylate. Preferred salt mixtures of the present invention include, e.g., R,R'-atracurium perchlorate, R,R'-atracurium tetrafluoroborate, R,R'-atracurium fluorosulfonate, R,R'-atracurium chloride and R,R'-atracurium bromide. The isomerically enriched R,R'-atracurium salt mixtures may be used to prepare cisatracurium salt, e.g., cisatracurium besylate.

The isomerically enriched salt mixtures of the present invention can be isolated in highly pure form, e.g., having chemical purity of at least about 95%, and preferably having purity of at least about 99%. The isomerically enriched salt mixtures of the present invention preferably have an isomeric purity of at least about 95%, and more preferably have an isomeric purity of at least about 99%, as measured by HPLC.

The present invention also provides a process for preparing isomerically enriched R,R'-atracurium salt mixtures which contain other isomers, particularly 1R-cis,1'R-trans and 1R-trans,1'R-trans isomers. The process preferably includes:

(a) admixing a salt mixture of R,R'-atracurium (e.g., R,R'-atracurium besylate or R,R'-atracurium chloride) with an acid;

(b) isolating an isomerically enriched salt mixture of R,R'-atarcurium; and (c) optionally purifying the isomerically enriched salt mixture.

Preferably, the process further includes converting the isomerically enriched salt mixture, which is at least one anion selected from perchlorate, tetrafluoroborate, fluorosulfonate, chloride and bromide, into a highly pure form of cisatracurium besylate by replacing the anion of the isomerically enriched R,R'-atracurium salt mixture with the cisatracurium besylate isomer, e.g., by subjecting the R,R'-atracurium salt mixture to ion exchange or solid phase extraction conditions in the presence of the anion, to produce a besylate salt of cisatracurium.

DETAILED DESCRIPTION OF THE INVENTION

The present invention provides novel, stable, isomerically enriched R,R'-atracurium salt mixtures that are useful, e.g., as intermediates for preparing highly pure cisatracurium besylate. Preferred salt mixtures of the present invention include, e.g., R,R'-atracurium perchlorate, R,R'-atracurium tetrafluoroborate, R,R'-atracurium fluorosulfonate, R',R-atracurium chloride and R,R'-atracurium bromide. The isomerically enriched R,R'-atracurium salt mixtures may be used to prepare cisatracurium salts, e.g., cisatracurium besylate.

The term isomerically enriched R,R'-atracurium salt mixtures of the present invention refers to R,R'-atracurium salts, which are not substantially free from other geometrical and/or optical isomers, that are contained in such R,R'-atracurium salts, that is, the R,R'-atracurium salt mixtures include greater amounts of e.g., the un-wanted 1R-cis,1'R-trans and 1R-trans,1'R-trans isomers.

Preferably, the isomerically enriched salts of the present invention have an isomeric purity of at least about 95%, and more preferably have an isomeric purity of at least about 99%, as measured by HPLC.

The isomerically enriched R,R'-atracurium salts of the present invention can be isolated in highly pure form, e.g., having chemical purity of at least about 95%, and preferably having purity of at least about 99%.

The term cisatracurium salt, e.g., cisatracurium besylate, as defined herein, refers to a salt of (1R,1'R,2R,2'R)-2,2'-[1,5-pentanediylbis[oxy(3-oxo-3,1-propanediyl)]]bis[1-(3,4-dimethoxyphenyl)methyl]-1,2,3,4-tetrahydro-6,7-dimethoxy-2-methylisoquinolinium e.g., the dibenzenesulfonate salt, which contains less then 1% of other geometrical and/or optical isomers, e.g., the 1R-cis,1'R-trans and 1R-trans,1'R-trans isomers.

The isomerically enriched salt mixtures of the present invention can be converted into highly pure cisatracurium besylate and, thus, can serve as useful intermediates for the production of highly pure (e.g., containing less then 1% of other geometrical and/or optical isomers) cisatracurium besylate.

The isomerically enriched salt mixtures of the present invention can be readily purified using simple purification techniques such as, e.g., crystallization and/or slurrying, thus avoiding the use of other tedious and expensive techniques, such as chromatography.

Figure 1:
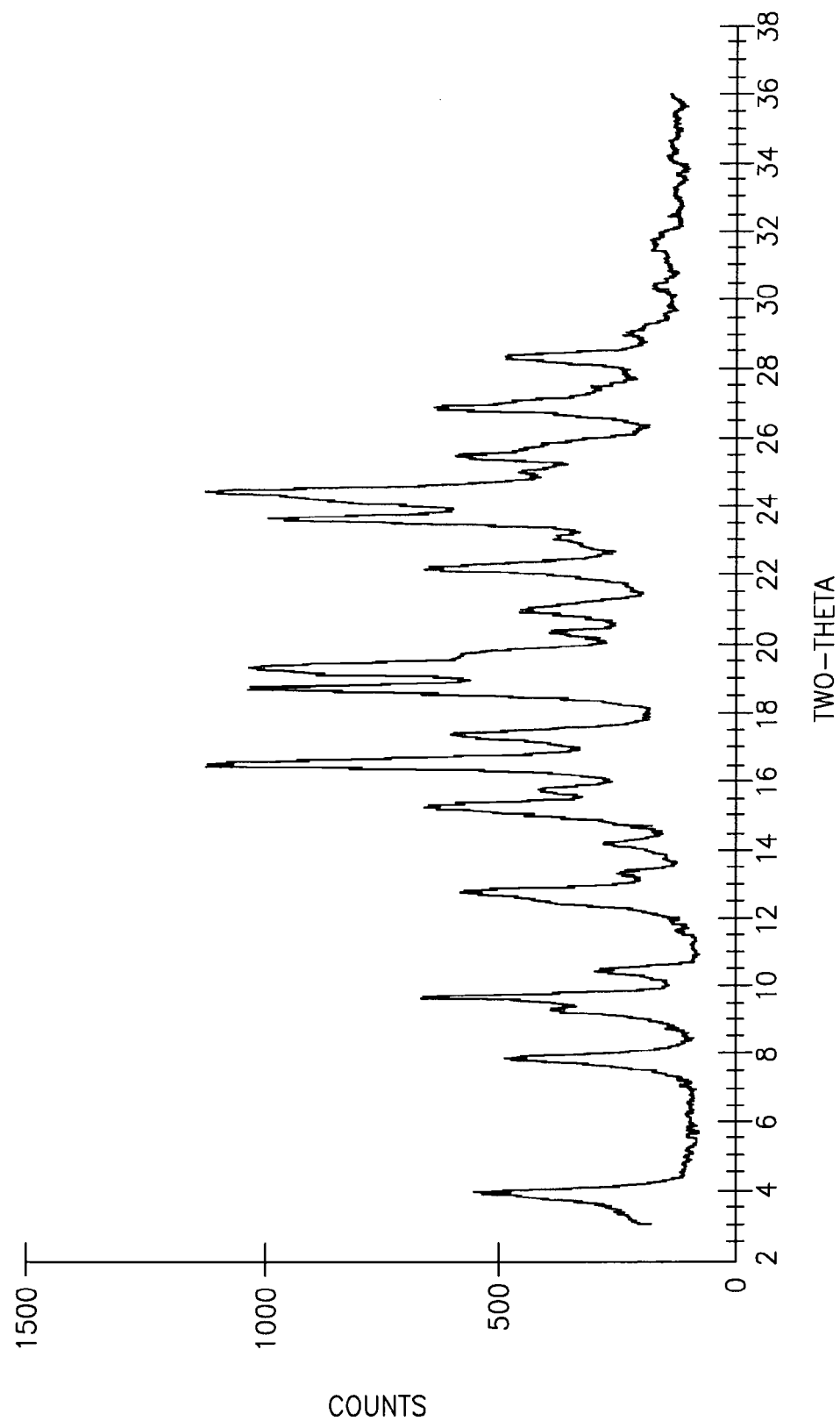
FIG. 1 depicts an X-ray powder diffraction (XRPD) pattern of R,R'-atracurium perchlorate.

The R,R'-atracurium perchlorate of the present invention can exist in the form of a crystalline solid, which preferably produces an X-ray powder diffraction pattern as depicted in FIG. 1. A peak listing for the X-ray powder diffraction pattern is provided in Table 1.

TABLE 1

R,R'-atracurium perchlorate - X-ray powder diffraction peak position and intensities

| Peak position 2θ degrees | Relative intensity $I/I_0$ |
|---|---|
| 4.0 | 42 |
| 7.9 | 41 |
| 9.3 | 31 |
| 9.7 | 59 |
| 10.4 | 22 |
| 12.8 | 48 |
| 13.3 | 14 |
| 14.2 | 16 |
| 15.3 | 52 |
| 15.8 | 27 |
| 16.6 | 100 |
| 17.4 | 46 |
| 18.8 | 89 |
| 19.4 | 85 |
| 19.7 | 40 |
| 20.4 | 24 |
| 21.0 | 29 |
| 22.2 | 49 |
| 23.1 | 22 |
| 23.7 | 86 |
| 24.5 | 95 |
| 25.0 | 28 |
| 25.5 | 43 |
| 26.9 | 47 |
| 28.4 | 36 |
| 29.0 | 10 |
| 30.3 | 5 |
| 31.5 | 5 |

The strong diffraction peaks at 4.0, 7.9, 9.3, 9.7, 12.8, 15.3, 15.8, 16.6, 17.4, 18.8, 19.4, 19.7, 21.0, 22.2, 23.7, 24.5, 25.0, 25.5, 26.9 and 28.4±0.2 degrees 2θ, are characteristic of this form of R,R'-atracurium perchlorate.

Figure 2:
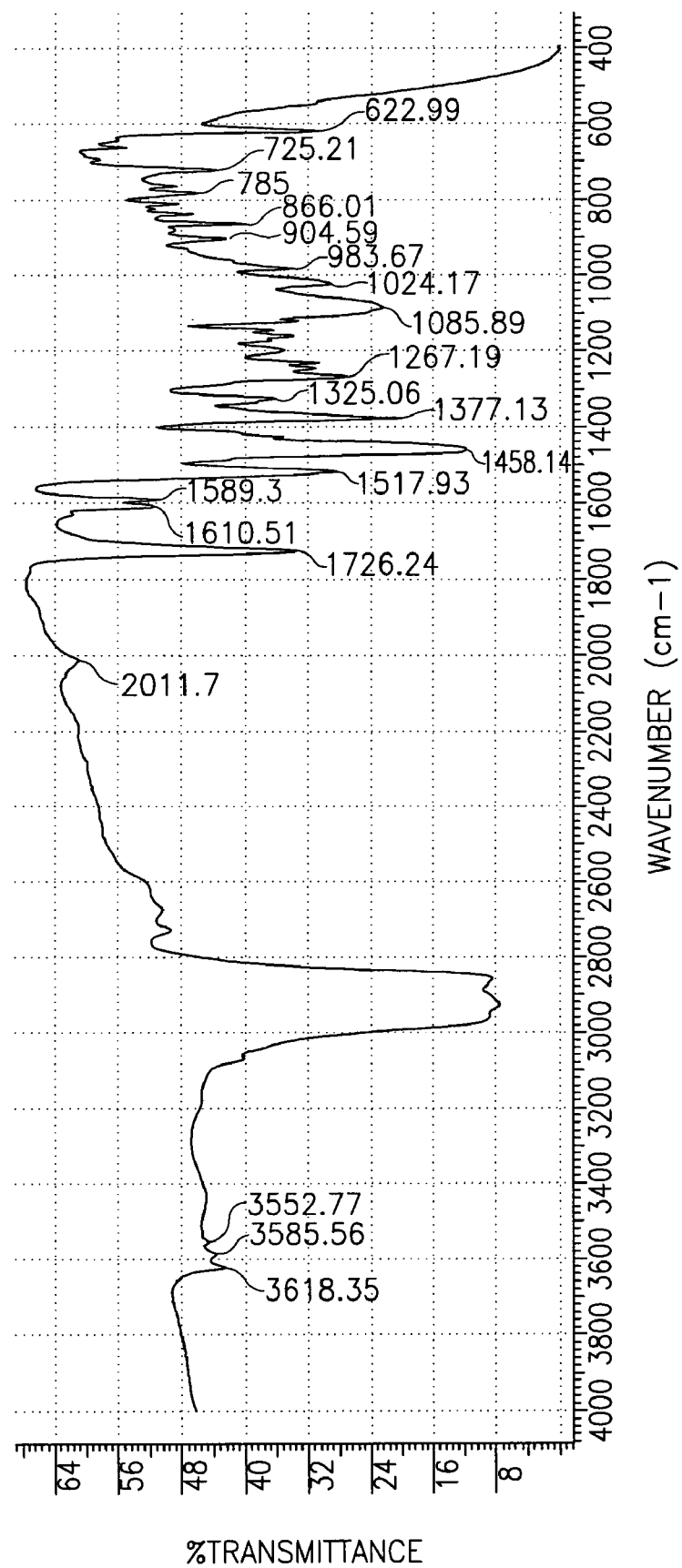
FIG. 2 depicts an Infra-red (IR) spectrum of R,R'-atracurium perchlorate.
Figure 3:
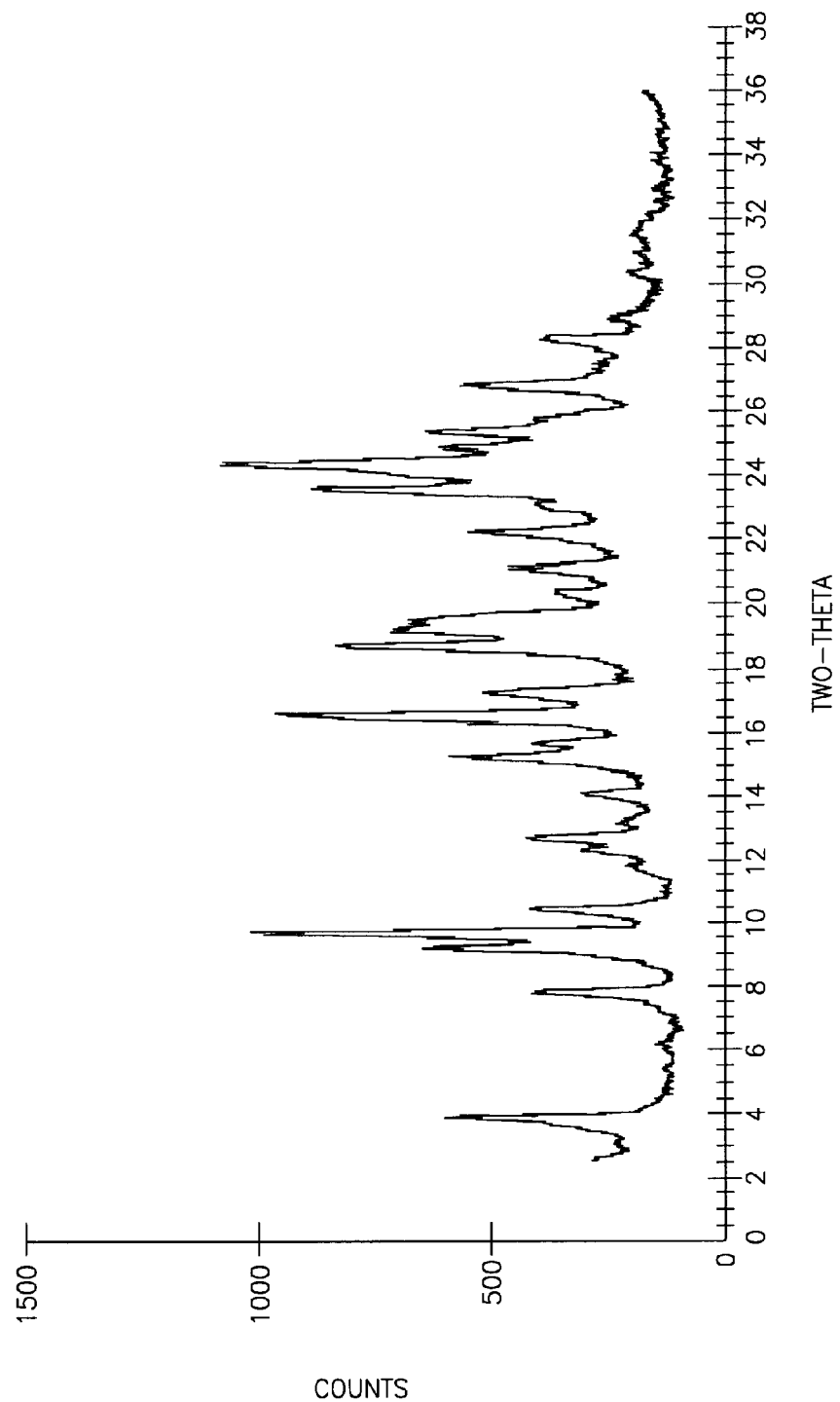
FIG. 3 depicts an X-ray powder diffraction (XRPD) pattern of R,R'-atracurium tetrafluoroborate.

A characteristic Infra-red (IR) spectrum of R,R'-atracurium perchlorate is depicted in FIG. 2. Characteristic bands are at: 623, 725, 785, 866, 905, 984, 1024, 1086, 1267, 1325, 1377, 1458, 1518, 1589, 1611, 1726, 2112, 3553, 3586, and 3618 cm$^{-1}$ The R,R'-atracurium tetrafluoroborate of the present invention can exist in the form of a crystalline solid, which preferably produces an X-ray powder diffraction pattern as depicted in FIG. 3. A peak listing for the X-ray powder diffraction pattern is provided in Table 2.

TABLE 2

R,R'-atracurium tetrafluoroborate - X-ray powder diffraction peak position and intensities

| Peak position 2θ degrees | Relative intensity I/I$_0$ |
|---|---|
| 3.9 | 46 |
| 6.2 | 4 |
| 7.8 | 34 |
| 9.2 | 59 |
| 9.7 | 100 |
| 10.4 | 33 |
| 11.8 | 10.6 |
| 12.3 | 19 |
| 12.7 | 32 |
| 13.2 | 11 |
| 14.1 | 17 |
| 15.3 | 48 |
| 15.7 | 23 |
| 16.6 | 87 |
| 17.3 | 37 |
| 18.7 | 69 |
| 19.2 | 57 |
| 20.4 | 19 |
| 21.1 | 30 |
| 22.2 | 38 |
| 23.1 | 23 |
| 23.6 | 78 |
| 24.3 | 95 |
| 24.9 | 45 |
| 25.3 | 49 |
| 26.8 | 42 |
| 28.2 | 26 |
| 28.8 | 11 |
| 30.4 | 7 |
| 31.0 | 6 |
| 31.5 | 6 |

The strong diffraction peaks at 3.9, 7.8, 9.2, 9.7, 10.4, 12.7, 15.3, 16.6, 17.3, 18.7, 19.2, 21.1, 22.2, 23.6, 24.3, 24.9, 25.3, 26.8 and 28.2±0.2 degrees 2θ, are characteristic of this form of R,R'-atracurium tetrafluoroborate.

Figure 4:
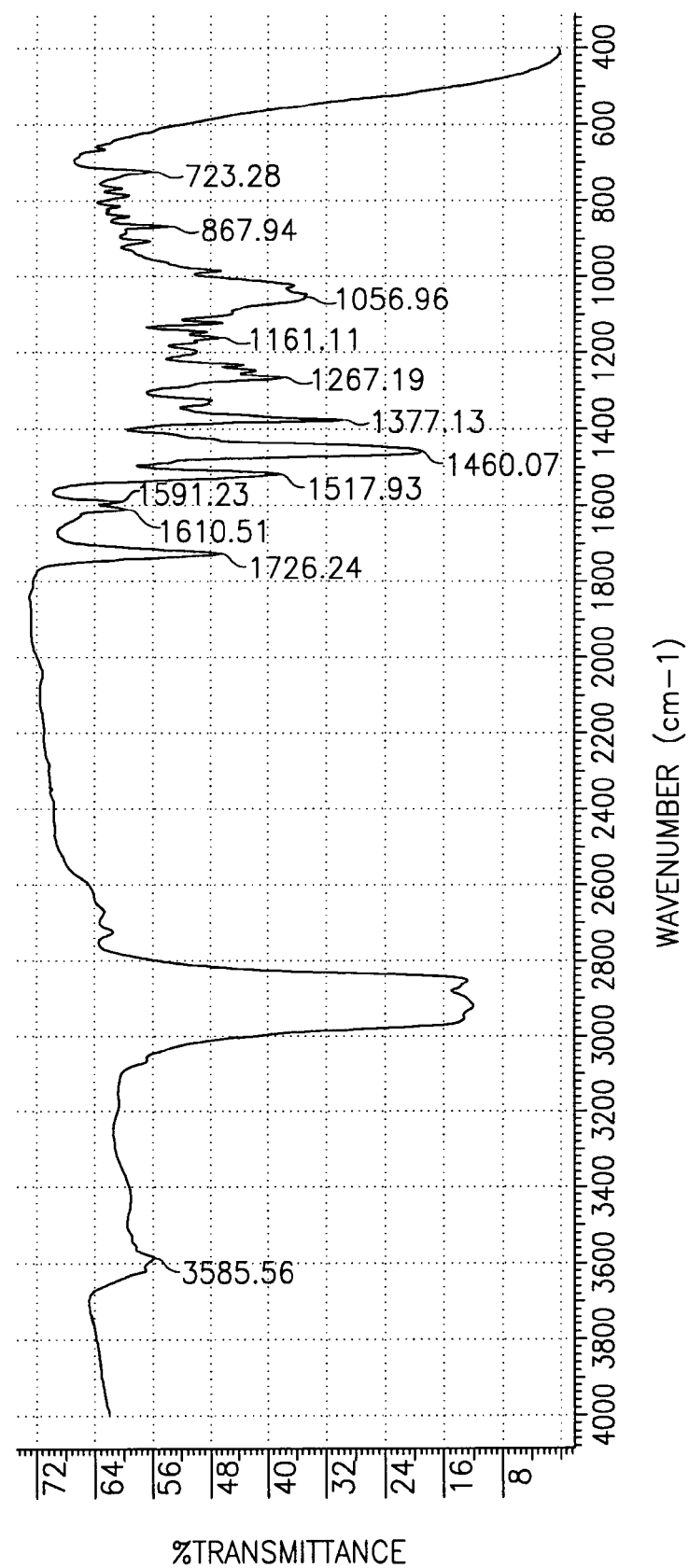
FIG. 4 depicts an Infra-red (IR) spectrum of R,R'-atracurium tetrafluoroborate.

A characteristic Infra-red (IR) spectrum of R,R'-atracurium tetrafluoroborate is depicted in FIG. 4. Characteristic bands are at: 723, 868, 1057, 1611, 1267, 1377, 1460, 1518, 1591, 1611, 1726, and 3586 cm$^{-1}$.

The present invention also provides a process for preparing isomerically enriched R,R'-atracurium salt mixtures which contain other isomers, particularly 1R-cis,1'R-trans and 1R-trans,1'R-trans isomers. The process preferably includes:
(a) admixing a salt of R,R'-atracurium (e.g., R,R'-atracurium besylate or R,R'-atracurium chloride) with an acid;
(b) isolating an isomerically enriched salt mixture of R,R'-atarcurium; and
(c) optionally purifying the isomerically enriched salt mixture.

In one embodiment, the anion in R,R'-atracurium salt isomer mixture (e.g., R,R'-atracurium besylate) is replaced by reacting the R,R'-atracurium salt (e.g., the besylate salt) isomer mixture with an acid form of the desired anion, preferably in a suitable solvent, to produce a salt mixture of R,R'-atracurium and the anion, and isolating the R,R'-atracurium salt mixture in isomerically enriched form, e.g., by precipitation. Preferably, the acid used as an anion source is an inorganic acid, which can include, e.g., tetrafluoroboric acid, perchloric acid and fluorosulfonic acid.

The resulting isomerically enriched R,R'-atracurium salt mixtures can be isolated by any suitable method, e.g., by precipitation. The precipitation can be carried out at a temperature of from about −10° C. to about 30° C. In some embodiments, the precipitation is carried out at a temperature of from about 0° C. to about room temperature.

The desired salt can be isolated by conventional methods such as, e.g., filtration or centrifugation.

Solvents, which can be used for reacting the starting R,R'-atracurium isomer mixture with an acid form of the desired anion include, e.g., tetrahydrofuran (THF), 2-methyl-tetrahydrofuran, acetone, methyl ethyl ketone (MEK), methyl isobutyl ketone (MIBK), and mixtures thereof. Preferred solvents, which can be used for reacting the R,R'-atracurium isomer mixture with an acid form of the desired anion, include THF, acetone, and mixtures thereof.

The isomerically enriched R,R'-atracurium salt mixture can be isolated by any suitable method, e.g. evaporation, lyophilization, spray drying, and the like.

The isomerically enriched R,R'-atracurium salt mixtures of the present invention can be purified using any suitable technique such as, crystallization or slurrying in a suitable solvent, or any combination of such methods. Suitable solvents for slurrying and crystallizing include, e.g., tetrahydrofuran (THF), acetone, dioxane, diethyl ether, methyl ethyl ketone, ethyl acetate and mixtures thereof.

Preferably, the process for preparing isomerically enriched R,R'-atracurium salt mixtures further includes converting the isomerically enriched salt mixture, which is at least one anion selected from perchlorate, tetrafluoroborate, fluorosulfonate, chloride and bromide into a highly pure form of cisatracurium besylate by replacing the anion of the isomerically enriched R,R'-atracurium salt mixture with the cisatracurium besylate isomer. Transforming one or more R,R'-atracurium salt mixtures of the present invention into cisatracurium besylate can be carried out using any suitable method, which can include, e.g., reacting an isomerically enriched R,R'-atracurium salt mixture of the present invention with a salt of benzenesulfonic acid, or by subjecting the isomerically enriched R,R'-atracurium salt mixture to ion exchange conditions, solid phase extraction, or any suitable combination of such methods, to replace the anion with besylate. As demonstrated in the experimental section of the present invention (e.g., examples 7b and 9 respectively) the isomer ratio is either retained or improved while converting the anion to besylate.

In one embodiment, the anion of the isomerically enriched R,R'-atracurium salt mixture (e.g., the tetrafluoroborate anion of isomerically enriched R,R'-atracurium tetrafluoroborate) is replaced with besylate by contacting the salt with an ion exchange resin, to produce highly pure cisatracurium besylate. An exemplary ion exchange process includes dissolving an isomerically enriched R,R'-atracurium salt mixture of the present invention in a solvent containing water, e.g., acetonitrile, methanol or a mixture thereof, and applying the solution to an ion exchange resin carrying the besylate ion. The resulting mixture optionally can be passed through a C18 cartridge to remove excess anion(s).

In another embodiment, the anion of the isomerically enriched R,R'-atracurium salt mixture (e.g., the tetrafluoroborate anion of isomerically enriched R,R'-atracurium tetrafluoroborate) also is replaced by reacting the R,R'-atracurium salt mixture with a salt of benzenesulfonic acid, e.g., calcium besylate, to produce highly pure cisatracurium besylate. An exemplary process includes dissolving an isomerically enriched R,R'-atracurium salt mixture of the present invention in an aqueous solution of a salt of benzene sulfonic acid, e.g., calcium besylate, adding water, and extracting with a first solvent. The first solvent can include, e.g., n-butanol, n-pentanol, isoamyl alcohol, 3-methyl-3-pentanol, cyclohexanol, or a mixture thereof. A preferred first solvent is n-butanol. After evaporating the first solvent, a second solvent can be added to precipitate the excess calcium besylate. The second solvent can include, e.g., diethyl ether, diisopropyl ether, dichloromethane, chloroform, and the like, or a mixture thereof. A preferred second solvent is dichloromethane.

In yet another embodiment, the anion of the isomerically enriched R,R'-atracurium salt mixture (e.g., the tetrafluoroborate anion of isomerically enriched R,R'-atracurium tetrafluoroborate) is replaced by solid phase extraction, to produce highly pure cisatracurium besylate. An exemplary solid phase exaction process includes preparing a solution of an isomerically enriched R,R'-atracurium salt mixture of the present invention with an aqueous solution of a salt of benzenesulfonic acid (e.g., calcium besylate), transferring the solution through a preconditioned stationary phase (e.g., C18 cartridge) followed by eluting with at least one solvent and evaporating the solvent. Suitable solvents for eluting can include, e.g., acetonitrile, methanol, ethanol, dichloromethane, chloroform, and mixtures thereof.

The resulting cisataracurium besylate can be isolated by any suitable method, e.g., evaporation, lyophilization, spray drying or any suitable combination of such methods.

The process of the present invention preferably produces cisatracurium besylate in an isomeric purity of at least about 95%, and more preferably in an isomeric purity of at least about 99%, as measured by HPLC. The cisatracurium besylate produced in accordance with the process of the present invention also preferably contains less than about 1% of other isomers, as measured by HPLC.

The following examples further illustrate the invention but, of course, should not be construed as in any way limiting its scope.

EXAMPLES

The isomer ratio as defined herein, e.g., isomer ratio of 58:36:6 (example 1(a)), refers to the isomer ratio of 1R-cis, 1'R-cis isomer:1R-cis,1'R-trans isomer:1R-trans,1'R-trans isomer respectively.

Example 1

This example demonstrates the purification of R,R-atracurium tetrafluoroborate.

1(a)—Precipitation from Tetrahydrofuran (THF)

R,R'-atracurium besylate mixture (2.01 g, isomer ratio ~58:36:6) was placed in a flask and 140 mL of THF was added. 600 µL of $HBF_4$ (48% in water) was added and the solution was stirred overnight, during which time a white solid was formed. The slurry was separated through a Buchner funnel to afford 461 mg (0.37 mmol, 39.5% yield from the cis isomer) of a white solid (isomer ratio ~78:20:2), melting point 133° C.

1(b)—Precipitation from THF/Acetone

R,R'-atracurium besylate mixture (500 mg, isomer ratio ~58:36:6) was placed in a 100 mL flask. 35 mL of THF was added to the solid followed by 3.5 mL of acetone. The mixture was stirred in an ice bath and $HBF_4$ (48% in water, 200 µL) was added and the solution was stirred for 5 hours in the ice bath, during which time a white solid was formed. The slurry was filtered through a Buchner funnel to afford 244.6 mg (0.197 mmol, 84.5% yield from the cis isomer) of a white solid (isomer ratio ~89:10.5:0.5).

1(c)—Precipitation from THF/acetone

R,R'-atracurium besylate (100 mg, 94.8% purity) was placed in a vial. 7 mL of THF and 0.7 mL of acetone were added to the solid. The reaction mixture was stirred in an ice bath and $HBF_4$ (48% in water, 40 µL, 1.25 eq.) was added and the solution was stirred for 5 hours in the ice bath, during which time a white solid was formed. The slurry was separated through a Buchner funnel to afford 39.2 mg (39.2% yield) of a white solid, having 97.2% purity.

1(d)—Re-Slurrying in THF/Acetone

Crude R,R'-atracurium tetrafluoroborate (244.6 mg, isomer ratio ~89:10.5:0.5) was placed in a 50 mL flask. 17 mL of THF followed by 1.7 mL of acetone were added to the white solid. The reaction mixture was stirred in an ice bath and $HBF_4$ (48% in water, 40 µL) was added and the slurry was stirred for 5 hours in the ice bath. The slurry was filtered through a Buchner funnel to afford 90.1 mg (0.0725 mmol, 41.9% yield from the cis isomer) of a white solid having 93:7:0 isomer ratio.

1(e)—Re-Slurrying in Methyl Ethyl Ketone (MEK)

R,R'-atracurium tetrafluoroborate (516.9 mg, isomer ratio ~97.3:2.7:0) was placed in a vial. 10 mL of methyl ethyl ketone was added to the solid. The reaction mixture was stirred at room temperature overnight. The slurry was filtered through a Buchner funnel yielding 448.1 mg (86.7% yield) of a white solid having 99.2:0.8:0 isomer ratio.

1(f) Re-Slurrying in THF/Acetonitrile

R,R'-atracurium tetrafluoroborate (524.5 mg, isomer ratio ~96.5:3.5:0) was placed in a flask. 280 mL of THF and 0.8 mL of acetonitrile were added to the solid. The reaction mixture was stirred at room temperature for the weekend. The slurry was filtered through a Buchner funnel to afford 516.9 mg (98.5% yield) of a white solid having 97.3:2.7:0 isomer ratio.

1(g) Crystallization

R,R'-atracurium besylate mixture (1 g, isomer ratio ~58:36:6) was placed in an Erlenmeyer. 20 mL of acetone was added to the solid to complete dissolution followed by 20 mL of THF. $HBF_4$ (48% in water, 350 µL) was added to the solution and the Erlenmeyer was kept in the refrigerator overnight. Ether (13.5 mL) was added to the solution and the solution was kept refrigerated for a month. The solid was filtered through a Buchner funnel to afford 8.6 mg (1.5% yield from the cis isomer) of needle shaped crystals (95:5:0 isomer ratio).

Example 2

This example demonstrates the purification of R,R'-atracurium perchlorate.

2(a)—Precipitation from THF/Acetone

R,R'-atracurium besylate mixture (100 mg, isomer ratio ~58:36:6) was placed in a vial. 7 mL of THF followed by 0.35 mL of acetone were added to the solid. The mixture was stirred in an ice bath and $HClO_4$ (70% in water, 8 µL, 1.1 eq.) was added and the solution was stirred for 5 hours in the ice bath, during which time a white solid was formed. The slurry was separated through a Buchner funnel to afford 25.8 mg (44.5% yield from the cis isomer) of a white solid (83.5: 15.5:1 isomer ratio), melting point 138° C.

2(b)—Precipitation from Methyl Ethyl Ketone

R,R'-atracurium besylate (100 mg, 93.8% purity) was placed in a vial. 2 mL of methyl ethyl ketone was added to the solid and the mixture was stirred in an ice bath. $HClO_4$ (70% in water, 10 µL, 1.25 eq.) was added and the solution was stirred for 4 hours in the ice bath, during which time a white solid was formed. The slurry was separated through a Buchner funnel to afford 35 mg (35% yield) of a white solid having 98.9% purity (by HPLC).

Example 3

This example demonstrates the purification of R,R'-atracurium fluorosulfonate.

R,R'-atracurium besylate mixture (200 mg, isomer ratio −58:36:6) was placed in a vial. 14 mL of THF was added to the solid followed by 1.4 mL of acetone. The reaction mixture was stirred in an ice bath. Fluorosulfonic acid (16 µL) was added and the solution was stirred for 5 hours in the ice bath, during which time a white solid was formed. The slurry was filtered through a Buchner funnel to afford viscous oil on the filter paper (69.5:27:3.5 isomer ratio).

Example 4

This example demonstrates the purification of R,R'-atracurium chloride.

R,R'-atracurium besylate mixture (0.8 g, isomer ratio −55.4:37.7:6.9) was placed in a vial. 30 mL of aqueous acidic solution (pH=2.5 with HCl) and 10 mL of acetonitrile were added to the solid. The solution was loaded on a pretreated ion exchange cartridge (conditioned with 200 mL of methanol and equilibrated with 200 mL of aqueous acidic solution (pH=2.5, HCl). The effluent, containing the R,R'-atracurium chloride mixture, was collected. 60 mL of aqueous acidic solution (pH=2.5 with HCl) was added and the solution was loaded on a preconditioned C18 cartridge (conditioned with 200 mL of acetonitrile and equilibrated with 200 mL of aqueous acidic solution (pH=2.5 with HCl)) and eluted with 50 mL of acetonitrile.

The solvent was removed by rotary evaporator to afford 510 mg of thick oil. The oil was dissolved in 5 mL of aqueous acidic solution (pH=3.5 with HCl) and lyophilized to afford 390 mg of the desired product (60.9:34.3:4.8 isomer ratio).

Example 5

This example demonstrates the preparation of R,R'-atracurium bromide.

R,R'-atracurium besylate mixture (0.8 g, isomer ratio −56.8:36.5:6.7) was placed in a vial. 30 mL of aqueous acidic solution (pH=3 with HBr) and 10 mL of acetonitrile were added to the solid. The solution was loaded on a pretreated ion exchange cartridge (conditioned with 200 mL of methanol, washed with 1 L of 0.1M HBr and equilibrated with 200 mL of aqueous acidic solution (pH=3 with HBO. The effluent, containing the R,R'-atracurium bromide mixture, was collected. 20 mL of aqueous acidic solution (pH=3 with HBr) was added and the solution was loaded on a preconditioned C18 cartridge (conditioned with 200 mL of acetonitrile and equilibrated with 200 mL of acidified water, pH=3 with HBr) and eluted with 50 mL of acetonitrile. The solvent was removed by rotary evaporator to afford thick oil. The oil was dissolved in 5 mL of aqueous acidic solution (pH=3 with HBr) and lyophilized to afford 444 mg of the desired product (57.4:36.6:6 isomer ratio).

Example 6

This example demonstrates the preparation of R,R'-atracurium besylate.

R,R'-atracurium tetrafluoroborate (0.5 g, isomer ratio −86.4:8.8:0.3) was placed in a vial. 50 mL of aqueous acidic solution (pH=3 with benzenesulfonic acid (BSA)) and 5 mL of acetonitrile were added to the solid. The solution was loaded on a pretreated ion exchange cartridge (conditioned with 200 mL of methanol, washed with 600 mL of 0.1M benzenesulfonic acid (BSA) and equilibrated with 200 mL of aqueous acidic solution (pH=3, BSA). The effluent, containing the cisatracurium besylate was collected. The solution was loaded on a preconditioned C18 cartridge (conditioned with 200 mL of acetonitrile and equilibrated with 200 mL of aqueous acidic solution, pH=2.5 with BSA) and eluted with 50 mL of acetonitrile. The solvent was removed by rotary evaporator to afford thick oil. The oil was dissolved in 5 mL of aqueous acidic solution (pH=3.5 with BSA) and lyophilized to afford 283.6 g (58% yield) of R,R'-atracurium besylate having isomer ratio of 87.5:6.7:0.2.

Example 7

This example demonstrates the conversion of R,R'-atracurium tetrafluoroborate into R,R'-atracurium besylate, followed by extraction with n-butanol.

7(a)—Preparation of Calcium Besylate Aqueous Solution 10 g of CaO (0.18 mol $Ca^{2+}$) was mixed with 100 mL water to afford a $Ca(OH)_2$ suspension. 56 g of benzenesulfonic acid (0.36 mol) was mixed with the thus formed suspension to form an aqueous solution of calcium besylate. The obtained solution was filtered, the pH was adjusted to 2.5 with benzenesulfonic acid and the volume was adjusted to 150 mL with water. The concentration of calcium besylate in the final solution was 43% (1.2M).

7(b) Preparation of R,R'-Atracurium Besylate 500 mg of R,R'-atracurium tetrafluoroborate (isomer ratio −96.6:0.4:0.6) was dissolved in mL of 1.2M calcium besylate aqueous solution. 50 mL of aqueous acidic solution (pH=3.0 with BSA) was added to the obtained solution, and the cisatracurium besylate was extracted 3 times with n-butanol (10 mL n-butanol was used for each extraction). The n-butanol phase (30 mL) was mixed with 300 mL cyclohexane and the solvents were evaporated to dryness at room temperature. The residual white precipitate was mixed with mL dichloromethane. The dichloromethane solution was filtered off and evaporated to afford thick oil. The oil was dissolved in 10 mL aqueous acidic solution (pH=3.0 with BSA) and lyophilized (isomer ratio −96.4:0.4:0.3).

Example 8

This example demonstrates the preparation of R,R'-atracurium besylate by solid phase extraction.

500 mg of R,R'-atracurium tetrafluoroborate (isomer ratio −86.7:8.8:0.9) was dissolved in 20 mL of 0.6M calcium besylate aqueous solution. The volume of the obtained solution was adjusted to 50 mL with aqueous acidic solution (pH=3.0 with BSA). 50 ml of R,R'-atracurium besylate solution was transferred through a preconditioned C18 cartridge and the cartridge was washed with 50 mL of aqueous acidic solution (pH=3.0 with BSA). The obtained effluent (100 mL) was analyzed by HPLC. The peak of R,R'-atracurium was not detected in the chromatogram (i.e. the sample was completely retained by the sorbent). The elution of the sample was started with acetonitrile (100 mL) and completed with 100 mL of ethanol, and then the solution was evaporated to afford oil. The oil was dissolved in 20 mL of an aqueous acidic solution (pH=3.0 with BSA) and mixed for 10 minutes with 20 mL of hexane. After phase separation, the aqueous phase, containing the R,R'-atracurium besylate, was lyophilized to afford 406 mg (72% yield) of a white powder (isomer ratio –86.0: 8.7:1.0).

Example 9

This example demonstrates the preparation of R,R'-atracurium besylate by solid phase extraction.

500 mg of R,R'-atracurium tetrafluoroborate (isomer ratio –86.4:8.7:0.9) was dissolved in 15 mL of 0.6M calcium besylate aqueous solution. The volume of the obtained solution was adjusted to 60 mL with aqueous solution (pH=3.0 with BSA). 60 ml of R,R'-atracurium besylate solution was transferred through the preconditioned C18 cartridge and the cartridge was washed with 250 ml of an aqueous acidic solution (pH=3.0, BSA). The obtained effluent (100 mL) was analyzed by HPLC. The peak of R,R'-atracurium was not detected in the chromatogram (i.e. the sample was completely retained by the sorbent). The elution of sample was carried out with dichloromethane (100 mL). The dichloromethane effluent, containing the R,R'-atracurium besylate and residual water, was mixed with 10 mL of aqueous acidic solution (pH=3.0 with BSA) and the solvent was evaporated. The obtained aqueous solution, containing the R,R'-atracurium besylate, was lyophilized to afford 324 mg (58% yield) of a white powder (isomer ratio –87.5:6.7:1.5).

Example 10

This example demonstrates the stability of the R,R'-atarcurium salts.

1 g of the R,R'-atracurium salt was placed in a closed vial, which was left aside at room temperature. From time to time the vial was opened and a sample was withdrawn and monitored by HPLC. The results are summarized in Table 3 and expressed as % content of the 1R-cis,1'R-cis isomer in the sample as function of the elapsed time, as measured by HPLC.

TABLE 3

| No. | R,R'-atracurium salt | Reference sample ($t_0$) | After 19 days | After 34 days | After 47 days |
|---|---|---|---|---|---|
| 1 | tetrafluoroborate | 98.2% | 88.8% | 85.3% | 82.6% |
| 2 | perchlorate | 98% | 92.1% | 92.7% | 92.3% |
| 3 | besylate | 97.2% | 80.5% | 15.1% | 7.9% |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing an isomerically enriched R,R'-atracurium salt, the process comprising:
    (a) admixing a salt of R,R'-atracurium with an acid;
    (b) isolating an isomerically enriched salt of R,R'-atracurium by precipitation or cystallization; and
    (c) optionally purifying the isomerically enriched salt;
wherein the isomerically enriched salt is enriched in the 1R-cis,1'R-cis isomer.

2. The process of claim 1, wherein the salt of R,R'-atracurium used for admixing with an acid is selected from R,R'-atracurium besylate, R,R'-atracurium perchlorate, R,R'-atracurium tetrafluoroborate, R,R'-atracurium fluorosulfonate, R,R'-atracurium chloride and R,R'-atracurium bromide.

3. The process of claim 1, wherein the anion of the R,R'-atracurium salt is replaced by contacting the R,R'-atracurium salt with an acid, which is at least one acid selected from tetrafluoroboric acid, perchloric acid and fluorosulfonic acid.

4. The process of claim 1, wherein the isolation comprises precipitating the isomerically enriched salt.

5. The process of claim 1, wherein the isomerically enriched salt is purified by slurrying in a solvent comprising tetrahydrofuran (THF), acetone, dioxane, diethyl ether, methyl ethyl ketone, ethyl acetate, or a mixture thereof.

6. The process of claim 5, wherein the isomerically enriched salt is purified by crystallizing the salt from a solvent comprising tetrahydrofuran (THF), acetone, dioxane, diethyl ether, methyl ethyl ketone, ethyl acetate or a mixture thereof.

7. The process of claim 1, wherein the purified isomerically enriched salt has at least one anion selected from perchlorate, tetrafluoroborate, and fluorosulfonate, and wherein the process further comprises converting the isomerically enriched salt into cisatracurium besylate.

8. The process of claim 7, wherein the conversion of the isomerically enriched salt into cisatracurium besylate comprises contacting the isomerically enriched salt with an ion exchange resin comprising a besylate ion, subjecting the isomerically enriched salt to solid phase extraction in the presence of a besylate ion, or any combination of such methods.

9. The process of claim 8, wherein the conversion comprises contacting an aqueous solution of the isomerically enriched R,R'-atracurium salt with a salt of benzenesulfonic acid, transferring the mixture through a stationary phase, eluting with at least one solvent, and evaporating the solvent.

10. The process of claim 9, wherein evaporating the solvent comprises freeze drying or spray drying.

11. The process of claim 10, wherein the obtained cisatracurium besylate has an isomeric purity of at least 99%.

12. An isomerically enriched R,R'-atracurium salt, which is R,R'-atracurium perchlorate, R,R'-atracurium tetrafluoroborate, or R,R'-atracurium fluorosulfonate.

13. The R,R'-atracurium salt of claim 12, which is R,R'-atracurium perchlorate.

14. The R,R'-atracurium salt of claim 13, wherein the X-ray powder diffraction (XRPD) pattern of the crystalline solid exhibits peaks at 4.0, 7.9, 9.3, 9.7, 12.8, 15.3, 15.8, 16.6, 17.4, 18.8, 19.4, 19.7, 21.0, 22.2, 23.7, 24.5, 25.0, 25.5, 26.9 and 28.4±0.2 degrees 2θ.

15. The R,R'-atracurium salt of claim 13, which exhibits characteristic Infra-red (IR) bands at: 623, 725, 785, 866, 905, 984, 1024, 1086, 1267, 1325, 1377, 1458, 1518, 1589, 1611, 1726, 2112, 3553, 3586, and 3618 cm-1.

16. The R,R'-atracurium salt of claim 12, which is R,R'-atracurium tetrafluoroborate.

17. The R,R'-atracurium salt of claim 16, wherein the X-ray powder diffraction pattern of the crystalline solid exhibits peaks at 3.9, 7.8, 9.2, 9.7, 10.4, 12.7, 15.3, 16.6, 17.3, 18.7, 19.2, 21.1, 22.2, 23.6, 24.3, 24.9, 25.3, 26.8 and 28.2±0.2 degrees 2θ.

18. The R,R'-atracurium salt of claim 16, which exhibits characteristic IR bands at: 723, 868, 1057, 1611, 1267, 1377, 1460, 1518, 1591, 1611, 1726, and 3586 cm-1.

\* \* \* \* \*